US00PP08106P

United States Patent [19]

van der Knapp

[11] Patent Number: Plant 8,106

[45] Date of Patent: Jan. 19, 1993

[54] CHRYSANTHEMUM PLANT—FUNSHINE CULTIVAR

[75] Inventor: Jacques C. M. van der Knapp, De Lier, Netherlands

[73] Assignee: Fides Beheer B.V., De Lier, Netherlands

[21] Appl. No.: 719,461

[22] Filed: Jun. 24, 1991

[51] Int. Cl.[5] ..... A01H 5/00

[52] U.S. Cl. ..... Plt./76

[58] Field of Search ..... Plt./74, 74.1, 82.1, Plt./82.4, 76, 77, 80

*Primary Examiner*—Howard J. Locker

*Attorney, Agent, or Firm*—Burns, Doane, Swecker & Mathis

[57] ABSTRACT

A new and distinct cultivar of Chrysanthemum plant named Funshine is provided. The new cultivar was the result of a controlled breeding program wherein an unnamed plant designated 83.598 was pollinated by the Penny Lane cultivar (U.S. Plant Pat. No. 6,238). More specifically, the new cultivar form attractive relatively small bicolored flowers wherein the petals are white and the disc florets particularly towards the center bear light-red coloration on the distal ends (as illustrated). The inflorescence tends to be pyramidal in configuration. The response period of the flowers is approximately seven and one-half weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Funshine.

The new cultivar is the product of a planned breeding program which had as its objective the creation of a new Chrysanthemum cultivar which exhibits attractive relatively small anemone bicolored flowers having a dark center (as illustrated), a flower response period of approximately seven and one-half weeks, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1985 at De Lier, The Netherlands. The female parent (i.e., the seed parent) was an unnamed plant designated 83.598 and the male parent (i.e., the pollen parent) was the Penny Lane cultivar (U.S. Plant Pat. No. 6,238). The parentage of the new cultivar can be summarized as follows:

83.598 × Penny Lane.

The seeds resulting from the above pollination were sown and plantlets were obtained which were physically and biologically different from each other. Selective study during September, 1985 resulted in the identification of a single plant of the new variety.

It was found that the new cultivar of the present invention:

(a) exhibits attractive relatively small anemone flowers having an overall diameter of approximately 40 mm. wherein the petals are white and the disc florets particularly towards the center bear light-red coloration on the distal ends, (b) bears flowers in a somewhat pyramidal configuration, (c) exhibits a flower response period of approximately seven and one-half weeks, (d) forms attractive dark green foliage, and (e) has the ability to produce flowers of commercially acceptable quality throughout the year in a cut mum production program.

Asexual reproduction of the new cultivar by cuttings initially taken during November, 1985, as performed at De Lier, The Netherlands, in a controlled environment has demonstrated that the characteristics of the new cultivar as herein disclosed are firmly fixed and are retained through successive generations of asexual propagation.

Funshine has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Penny Lane cultivar, the Funshine cultivar is found to exhibit a smaller flower size, more intense coloration at the flower center, more vigor, and a faster response period.

When the new cultivar of the present invention is compared to the Improved Funshine cultivar (U.S. Ser. No. 07/719,464, filed concurrently herewith), the Funshine cultivar is found to exhibit less vigor and less intense coloration at distal ends of the disc florets. When the new cultivar of the present invention is compared to the Funbeam cultivar (U.S. Ser. No. 07,719,463, filed concurrently herewith), it is noted that the Funbeam cultivar exhibits light red-purple petals, more intense coloration on the distal ends of the disc florets than the Funshine cultivar, and less intense coloration on the distal ends of the disc florets than the Improved Funshine cultivar. When the new cultivar of the present invention is compared to the Funrise cultivar (U.S. Ser. No. 07,719,465, filed concurrently herewith), it is noted that the Funrise cultivar exhibits red-purple petals which tend to be slightly darker than those of the Funbeam cultivar and tends to exhibits a slightly less intense light-red coloration on the distal ends of the disc florets than the Funshine cultivar. When the new cultivar of the present invention is compared to the Funset cultivar (U.S. Ser. No. 07,719,462, filed concurrently herewith), it is noted that the Funset cultivar exhibits very light-red petals and orange-red coloration on the distal ends of the disc florets. When the new cultivar of the present invention is compared to the Funglow cultivar (U.S. Ser. No. 07,720,211, filed concurrently herewith), it is noted that the Funglow cultivar exhibits yellow petals and greyed-purple coloration on the distal ends of the disc florets.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during December, 1990. The plants described were grown under standard greenhouse conditions which approximate those commonly utilized for the production of cut mums.

Classification:

*Botanical.*—*Chrysanthemum morifolium* Ramat., cv. Funshine.

*Commercial.*—Cut anemone spray.

INFLORESCENCE

A. Capitulum:

*Form.*—Pyramidal.

*Type.*—Anemone.

*Diameter across face.*—Approximately 40 mm. on average.

*Diameter of flower center.*—Approximately 25 mm. on on average.

B. Corolla of ray and disc florets:

*Color (General tonality from a distance of three meters).*—White with light-red center.

*Color ray florets (top surface).*—White, White Group 155D.

*Color disc florets.*—Light-red, Red Group 51B.

C. Reproductive organs:

*Androecium.*—Not present.

*Gynoecium.*—Present in both ray and disc florets.

PLANT

A. General appearance

*Height.*—Approximately 90 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Funshine, substantially as herein shown and described, which:

(a) exhibits attractive relatively small anemone flowers having an overall diameter of approximately 40 mm. wherein the petals are white and the disc florets particularly towards the center bear light-red coloration on the distal ends, (b) bears flowers in a somewhat pyramidal configuration, (c) exhibits a flower response period of approximately seven and one-half weeks, (d) forms attractive dark green foliage, and (e) has the ability to produce flowers of commercially acceptable quality throughout the year in a cut mum production program.

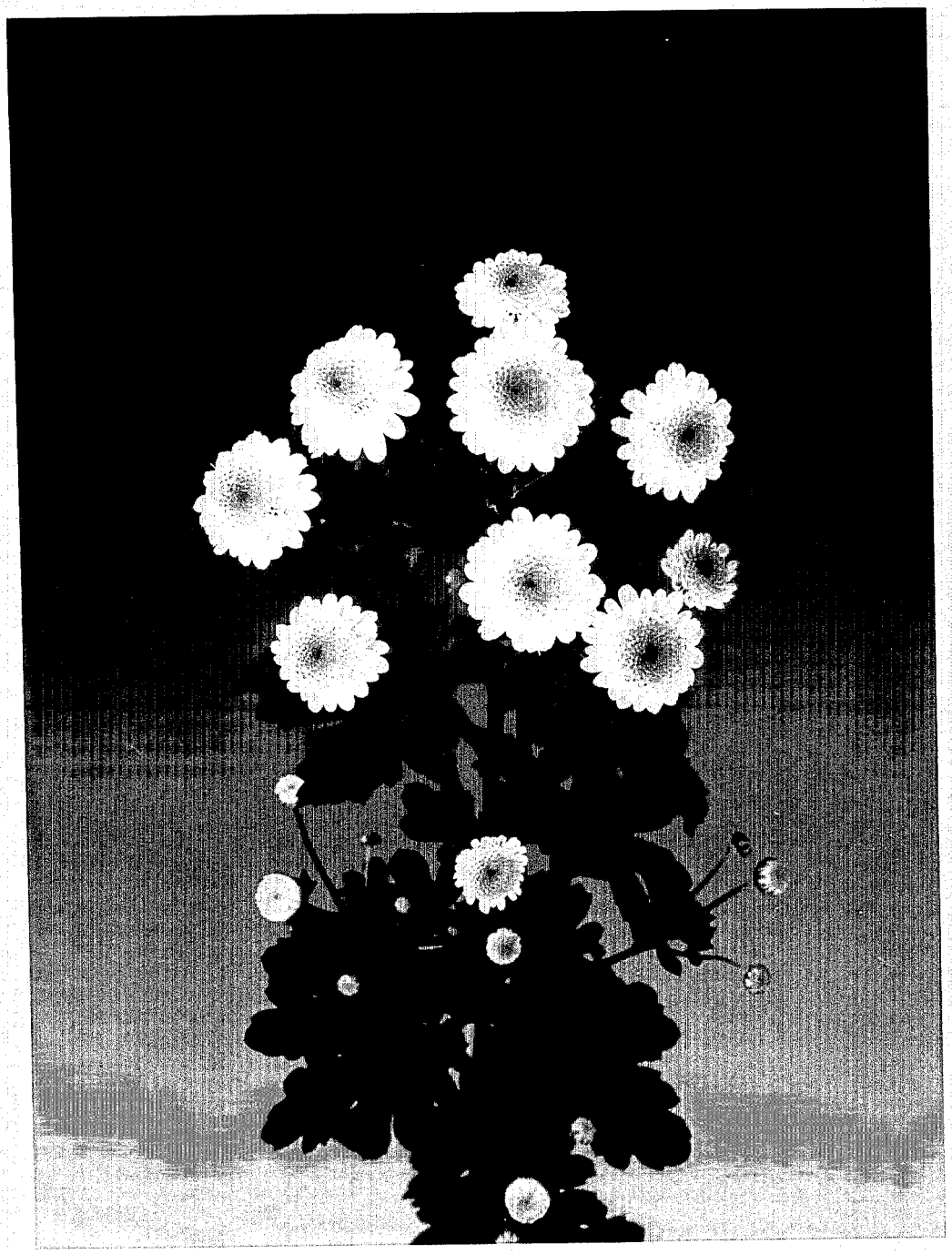

* * * * *